(12) United States Patent
Crawford et al.

(10) Patent No.: US 6,306,118 B1
(45) Date of Patent: Oct. 23, 2001

(54) NEEDLE HOLDER ASSEMBLY

(75) Inventors: Jamie Crawford, New York; Mark Newby, Tuxedo, both of NY (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 09/266,163

(22) Filed: Mar. 10, 1999

Related U.S. Application Data

(60) Provisional application No. 60/077,996, filed on Mar. 13, 1998.

(51) Int. Cl.[7] ............................... A61M 5/00; A61M 5/31
(52) U.S. Cl. .............................................. 604/243; 600/577
(58) Field of Search ..................................... 604/240, 192, 604/263, 242, 243, 264, 272; 600/573–584

(56) References Cited

U.S. PATENT DOCUMENTS 5,443,287 * 8/1995 Wells .
5,611,781 * 3/1997 Sircom et al. ........................ 604/164
5,616,136    4/1997 Shillington et al. .
5,755,673 * 5/1998 Kinsey .................................. 600/577
5,797,490 * 8/1998 Fujii ..................................... 206/365

FOREIGN PATENT DOCUMENTS 0 824 895 A1   2/1998  (EP) .

* cited by examiner

Primary Examiner—Sharon Kennedy
Assistant Examiner—Catherine Serke
(74) Attorney, Agent, or Firm—Nanette S. Thomas

(57) ABSTRACT

The present invention is a needle holder assembly for using during a blood collection procedure and more particularly to a blood collection tube holder with means for easily engaging and disengaging a blood collection needle from the holder and for not prematurely disengaging a blood collection needle. The needle holder includes an engaging trigger to engage the holder with a needle and a disengaging trigger to disengage the holder with a needle and a preventative needle release indicator that prevents premature movement of the disengaging trigger and disengagement of the needle from the holder.

6 Claims, 16 Drawing Sheets

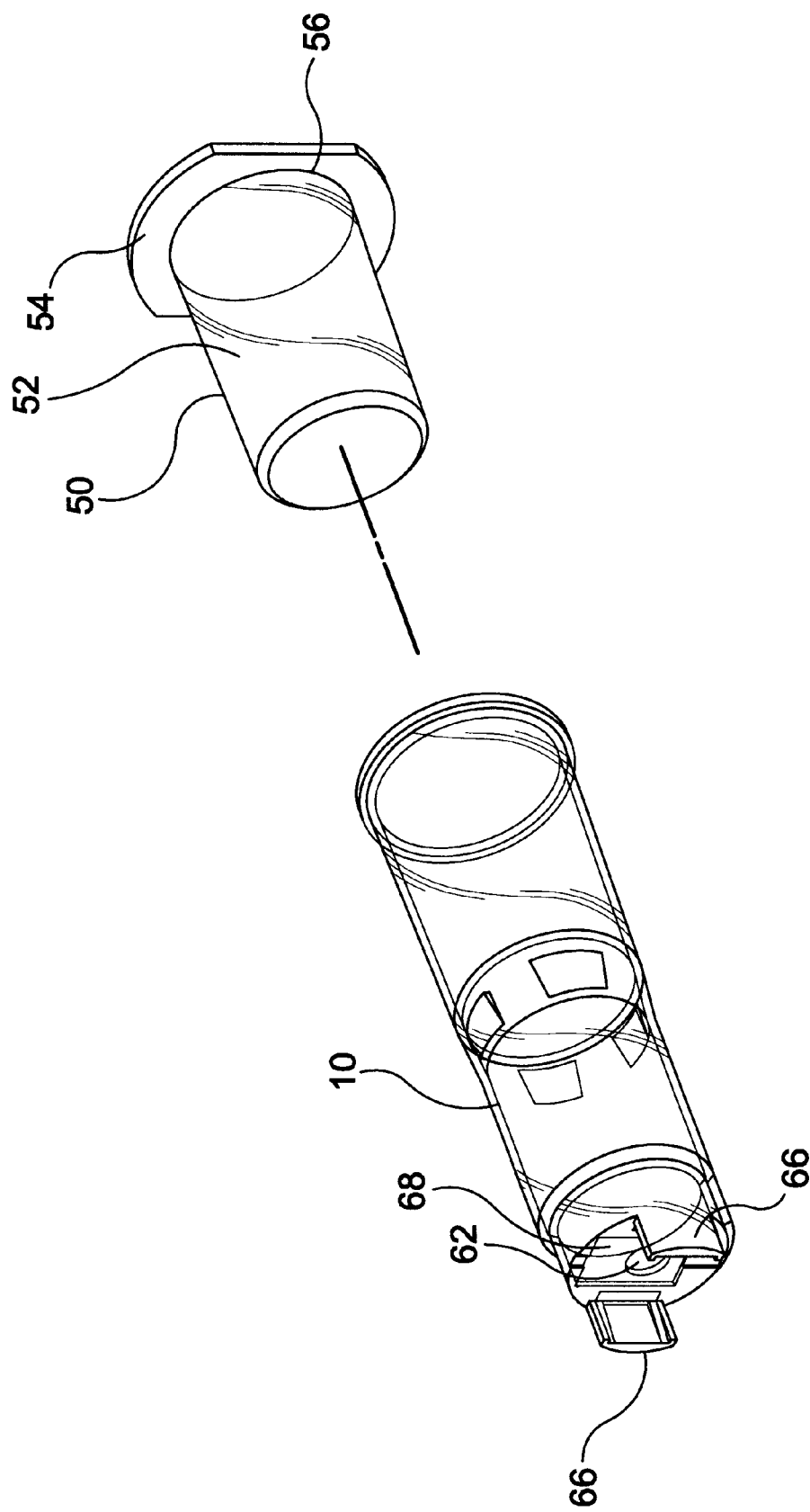

NEEDLE HOLDER ASSEMBLY

This application claims the benefit of U.S. Provisional Application No.: 60/077,996 Mar. 13, 1998.

BACKGROUND OF THE INVENTION

1. Field of the Invention

The present invention relates to needle holder assemblies for use during a blood collection procedure and more particularly to a blood collection tube holder with means for easily engaging and disengaging a blood collecting needle from the holder.

2. Description of Related Art

Conventional blood collection systems typically employ some form of a reusable holder on which detachable and disposable needles and fluid collection tubes may be mounted. A blood collection system of this nature can be assembled prior to use and then disassembled after use. Thus, these blood collection systems allow repeated use of the holder upon replacement of the disposable needle and/or fluid collection tube.

Conventional blood collection procedures involve venipuncture to draw blood into a blood collection tube using a doubled ended needle assembly and a holder for maintaining the needle assembly and the collection tube in a fixed relation. The conventional double ended needle assembly includes a hub having an intravenous needle extending in one direction and a non-patient needle extending in the other direction. The hub is threadedly engaged with the holder wherein the non-patient needle is located within the housing of the holder and the intravenous end of the needle extends forwardly from the holder for puncturing the vein of a patient. The housing of the holder is open to receive an evacuated blood collection tube having a stopper to penetrably receive the non-patient needle. To draw a blood sample from a patient using this assembly, the blood collection tube is fully inserted into the housing of the holder such that blood will be drawn through the needle and into the collection tube.

On completion of the procedure, the intravenous needle is withdrawn from the patient and the needle assembly is detached from the holder. The manner of the disposal of the needle assembly varies, depending upon the phlibotomist, the procedures to be followed and other considerations.

Many incurable or fatal diseases are transmissible through contact with the blood of an infected person. A needle used during a blood collection procedure obviously contains a quantity of blood. In the event of needle stick, infection from infected blood is possible. Considering that inadvertent needle stick occurs frequently, the degree of exposure of medical personnel to incurable or fatal diseases is possible.

Particularly in recent years, various devices have been developed to assist with safely engaging and disengaging the needle from a needle holder to minimize instances of needle stick and exposure to blood.

However, these holders are concerned with custom designed blood collecting needles that have a depression or raised part on the hub, unlike a conventional blood collecting needle. Therefore these holders are not compatible with conventional blood collecting needles. In addition the needle is not fixed in the holder by screw-meshing as a conventional blood collecting needle is, so they have the drawback that the fixing of the blood collecting needle in the holder becomes loose.

Other holders have been developed that have a needle fixed in the holder with a one touch type for engaging and disengaging the needle. However, these devices have the drawback whereby needles may be prematurely released from the holder while the needle is in the patient.

Therefore, there exists a need to provide a blood collecting needle holder: (i) that is compatible with conventional blood collecting needles; (ii) whereby the user can disengage the blood collecting needle from the holder without touching the needle; (iii) whereby the blood collecting needle maybe securely engaged with the needle holder without the possibility of premature release from the holder; (iv) that has tactile features whereby the user may be deterred from touching the needle, assist the user in orienting the needle with the patient and triggering the appropriate disengaging mechanisms; (v) that has visual features whereby the user may be deterred from touching the needle, assist the user in orienting the needle with the patient and triggering the appropriate disengaging mechanisms; and (vi) that holder is capable of operating effectively without the need for any additional components.

SUMMARY OF THE INVENTION

The present invention is a needle holder assembly comprising a holder, means for disengaging a conventional blood collecting needle from the holder, means for engaging a conventional blood collecting needle to the holder, and means for deterring the user from touching the needle, assisting the user in orienting the needle with the patient and preventing premature release of the needle from the holder.

Preferably, the holder comprises a tubular body comprising a top end, an open bottom end and a sidewall extending between the top end and the bottom end.

Preferably, the means for disengaging a conventional blood collection needle from the holder is a needle actuation mechanism located at the top end of the holder.

Preferably, the means for engaging a conventional blood collection needle to the holder is a threaded passageway in the needle actuation mechanism.

Preferably, the actuation mechanism comprises a disengaging trigger, an engaging trigger, a threaded passageway and a finger recess indicator. Most preferably, the triggers and indicator have distinct features that provide the user with visual and tactile means for distinguishing between them.

Most preferably, the needle actuation mechanism comprises first and second half female members or jaws with surfaces that cooperate to define the threaded passageway therebetween, an engaging trigger for cooperating the female members and a disengaging trigger for separating the female members and a finger recess indicator.

When the engaging trigger is activated, the jaws cooperate to a closed position to define a threaded passageway. A conventional needle assembly comprising a non-patient end, an intravenous end and a hub, is then screwed into the threaded passageway by the user whereby the non-patient end of the needle extends into the body of the holder and the intravenous end of the needle extends outwardly from the top end of the holder. To release and dispose of the needle from the holder, the holder is held over a sharps disposal container such that the intravenous end of the needle extends vertically from the holder, then the disengaging trigger is activated, whereby the female members are separated to an open or retracted position and so that the threaded passageway is interrupted and there is a gap which is greater than the cross section of the hub of the conventional needle assembly so that the needle assembly is released from the holder and into the sharps disposal container.

In use, a user will use one finger of one hand to close the actuation mechanism whereby the threaded passageway is available for engaging a conventional needle assembly. The user then screws into the threaded passageway a conventional needle assembly whereby the hub of the needle assembly is screwed into the threaded passageway and the intravenous end of the needle extends from the top end of holder and the non-patient end of the needle extends into the housing of the holder.

The intravenous end of the needle is then inserted into the patient's skin as guided by the finger recess indicator to the user. A fluid collection tube is then inserted into the holder in communication with the non-patient end of the needle.

In addition to guiding the user for proper orientation of the holder assembly relative to the user, the needle is prevented from being prematurely released from the actuation mechanism due to the finger recess indicator. The finger recess indicator prevents the patient's skin from activating the disengaging trigger or the actuation mechanism.

After use, the fluid collection tube is removed from the holder, the holder is positioned over a sharps disposal container and the disengaging trigger is depressed with one finger of the user whereby the threaded passageway is interrupted and there is a gap and the needle falls into the sharps disposal container under the force of gravity. During the disengaging procedure, the user is deterred from touching the needle by the finger recess indicator.

A significant advantage of the present invention as compared to previously available needle holder assemblies with an ejection capability is reduced cost. Since the present invention is compatible with conventional needle assemblies and conventional fluid collection tubes, holders in accordance with the present invention do not require the use of special or custom made needle assemblies and/or additional custom made components.

A further advantage of the present invention as compared to previously available needle holder assemblies is improved reliability and ease of operation.

Another notable advantage of the present invention is that because of the finger recess indicator, the user is physically deterred from touching the needle that is removably secured in the holder of the present invention. As such, the finger recess indicator substantially reduces the touch contamination potential that may be faced by the user that is associated with blood collecting needle holder assemblies.

Also notable is that the finger recess indicator of the present invention provides a tactile response and feedback to the user whereby when the user touches the finger recess indicator the user is alerted not to proceed past the finger recess indicator as compared with visual response and feedback.

In addition, the finger recess indicator provides the user with tackle identification of where the activation and reset positions of the assembly are located. For example, when the user touches the finger recess indicator, the user is alerted to the position of the holder and the needle with respect to the engaging or disengaging triggers. Therefore if the user is unable to visually look at the holder, the tactile response and feedback from the finger recess indicator will assist the user in properly identifying the engaging or disengaging triggers of the holder.

In addition, the engaging and disengaging triggers also provide a tactile response and feedback to the user. The finger guides associated with the triggers are distinct from one another so that the user is able to distinguish the engaging trigger from the disengaging trigger. Furthermore, the triggers provide the user with visual identification to distinguish the engaging trigger from the disengaging trigger.

Another notable attribute of the present invention is that the finger recess indicator prevents the disengaging trigger from prematurely being pushed by the user or the patient's skin. When the holder is in use in the patient's skin, the finger recess indicator provides a shield between the patient's skin and the disengaging trigger so that the needle is not prematurely released from the holder.

DESCRIPTION OF THE DRAWINGS

FIG. 15 is a perspective view of the components of the holder.

DETAILED DESCRIPTION

Figure 2:
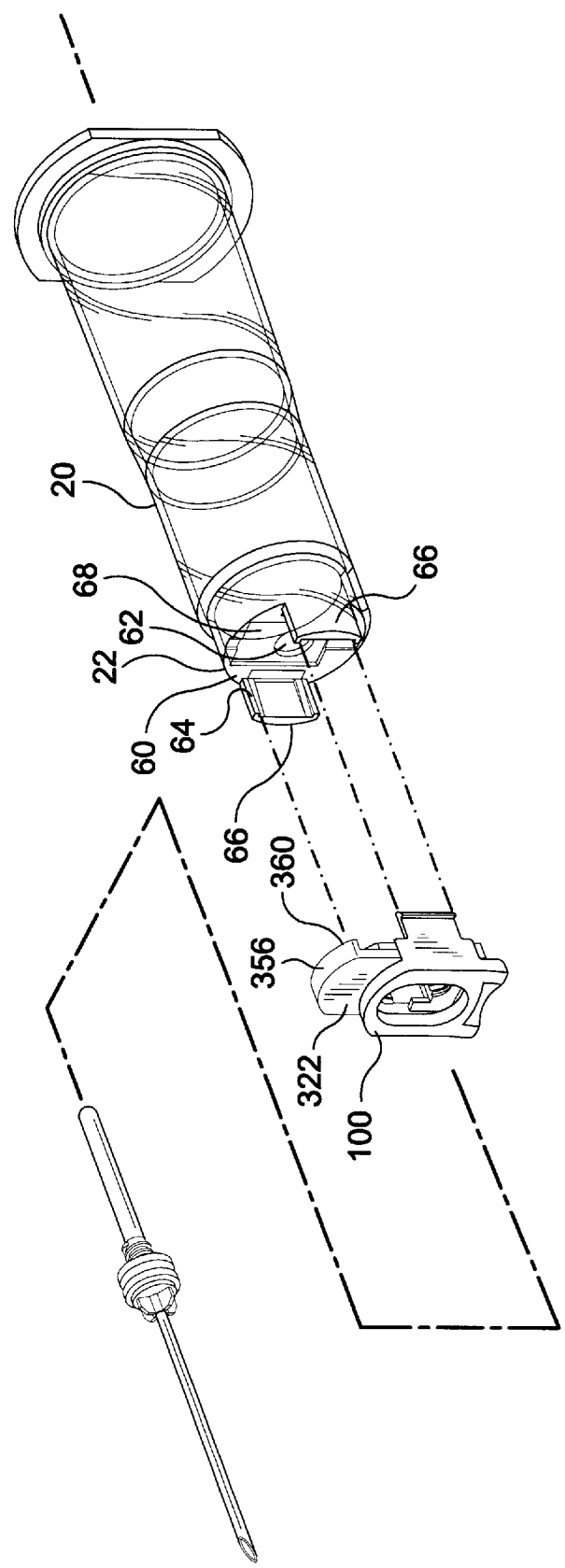
FIG. 2 is a perspective view of the holder and assembled actuation mechanism of the present invention.
Figure 3:
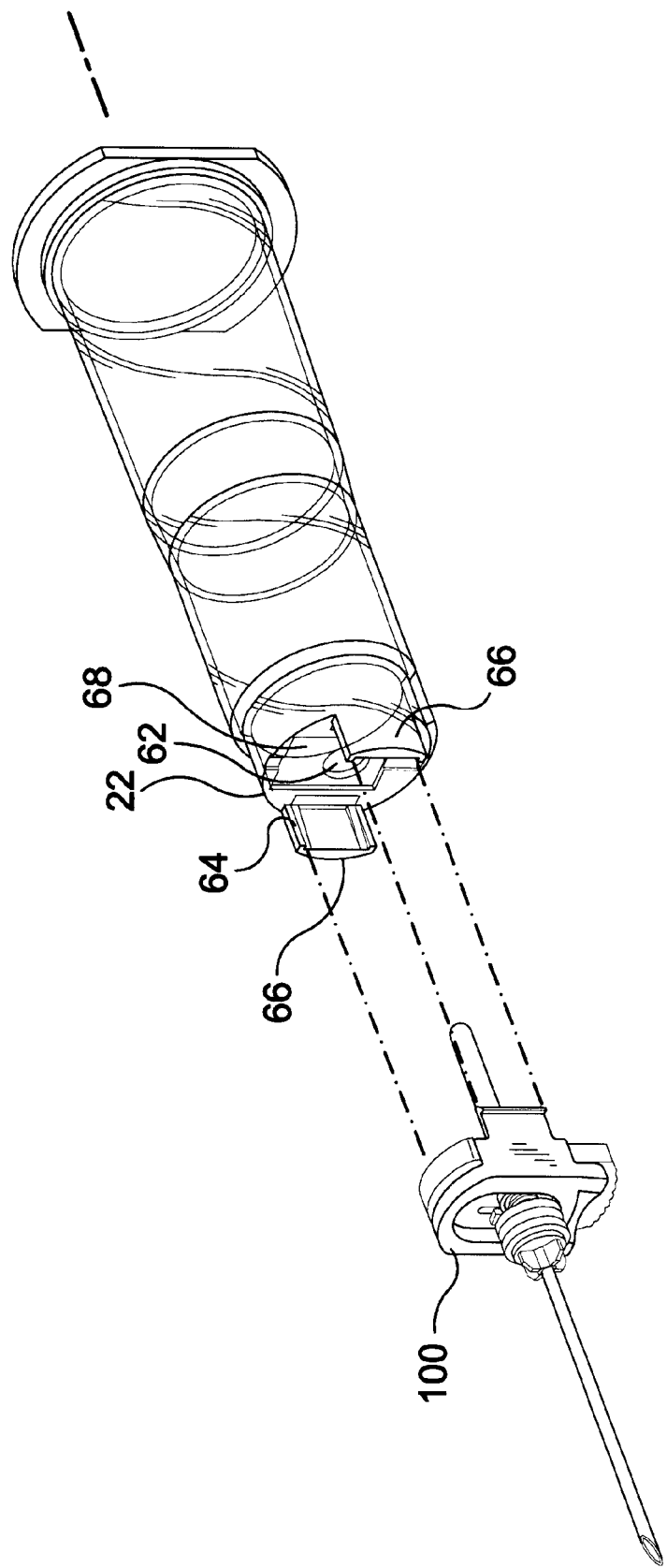
FIG. 3 is a perspective view of the holder and assembled actuated mechanism of the present invention with the needle assembly engaged with the actuation mechanism.
Figure 4:
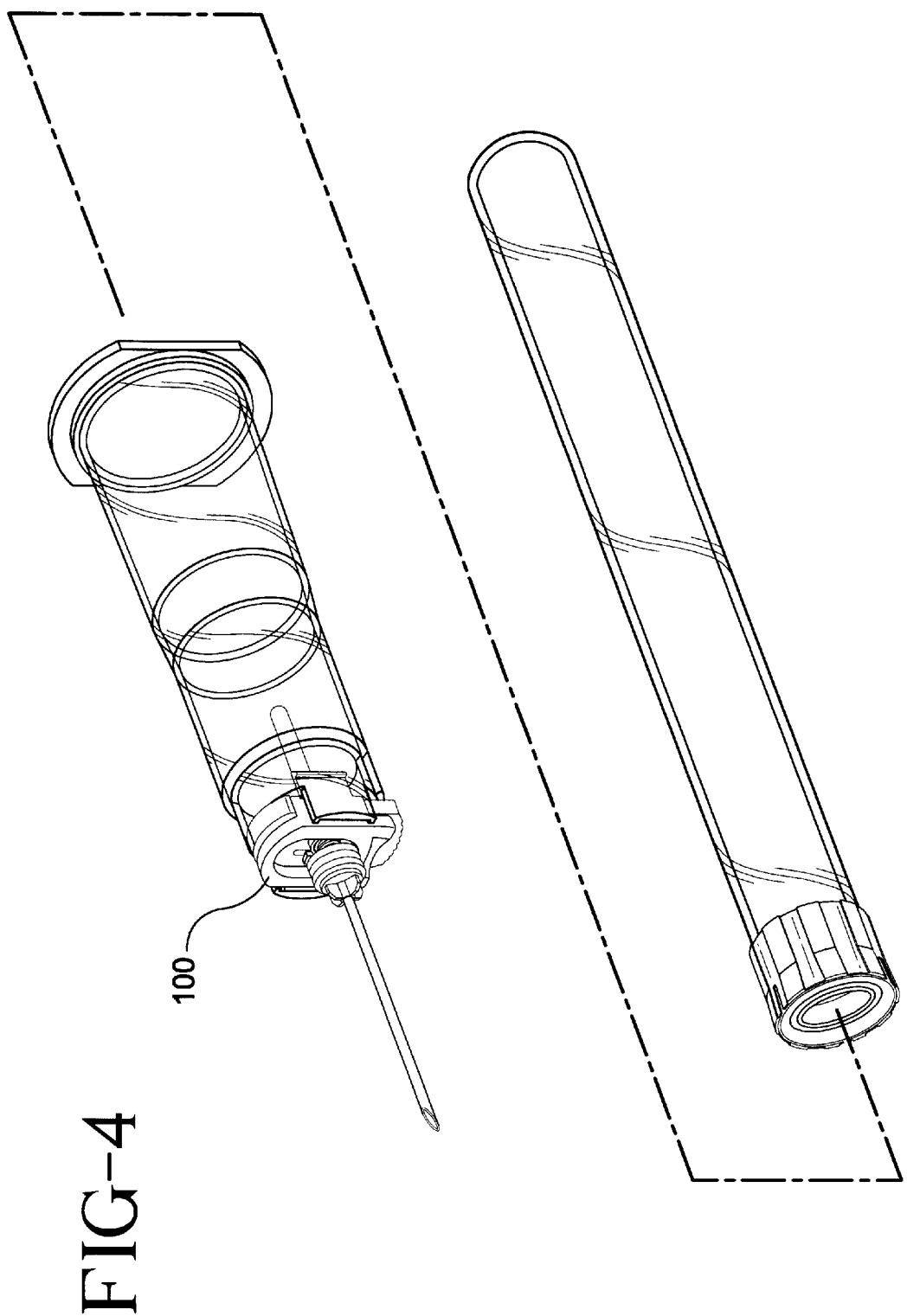
FIG. 4 is a perspective of the assembled holder and the actuator mechanism of the present invention with the needle assembly engaged with the actuation mechanism.

Referring to the drawings in which like reference characters refer to like parts throughout the several views thereof, in particular FIG. 2 illustrates a holder 10 for a blood collection needle comprising a housing 20 and an actuation mechanism 100.

Figure 1:
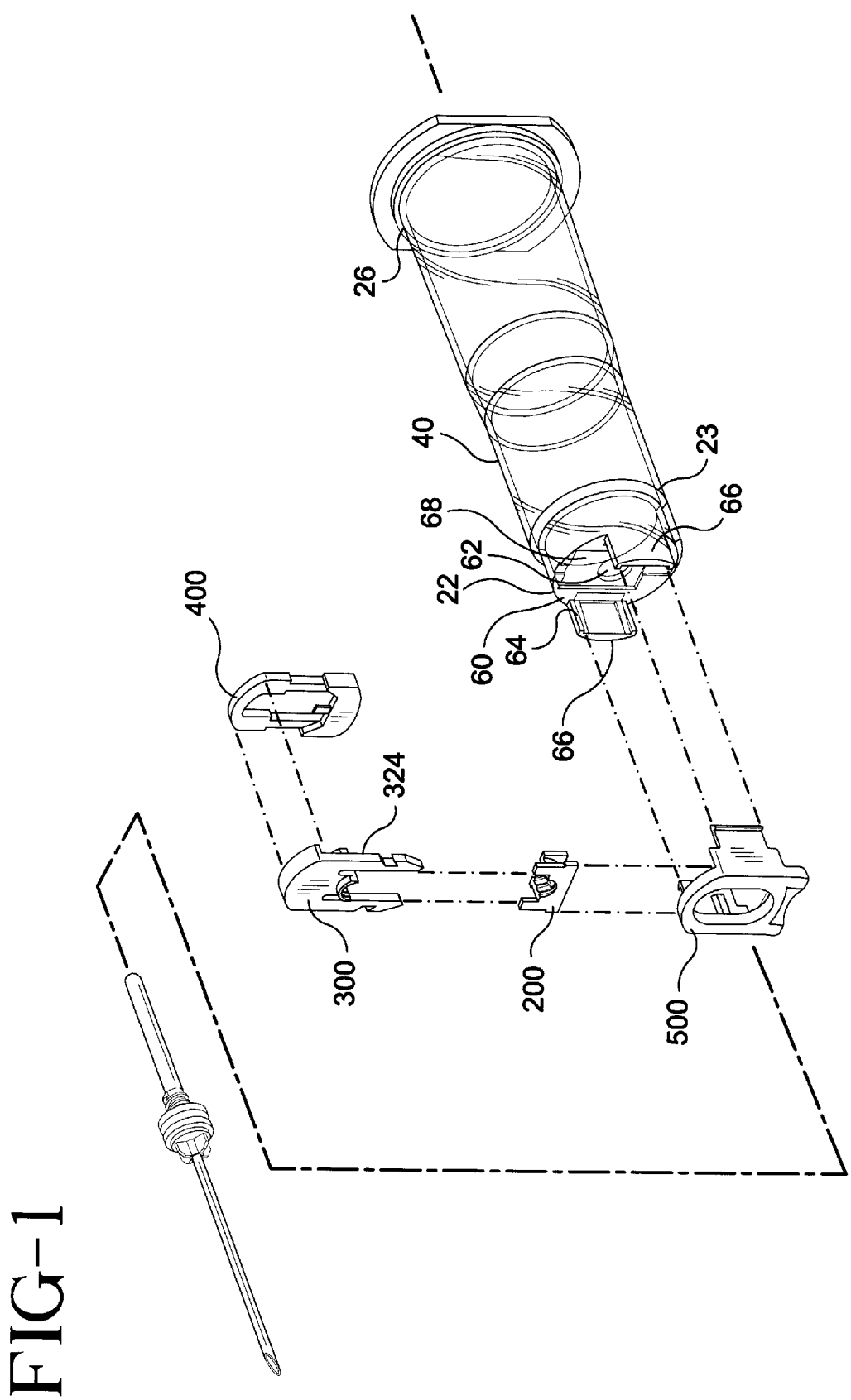
FIG. 1 is a perspective view of the unassembled holder and actuation mechanism of the present invention.
Figure 5:
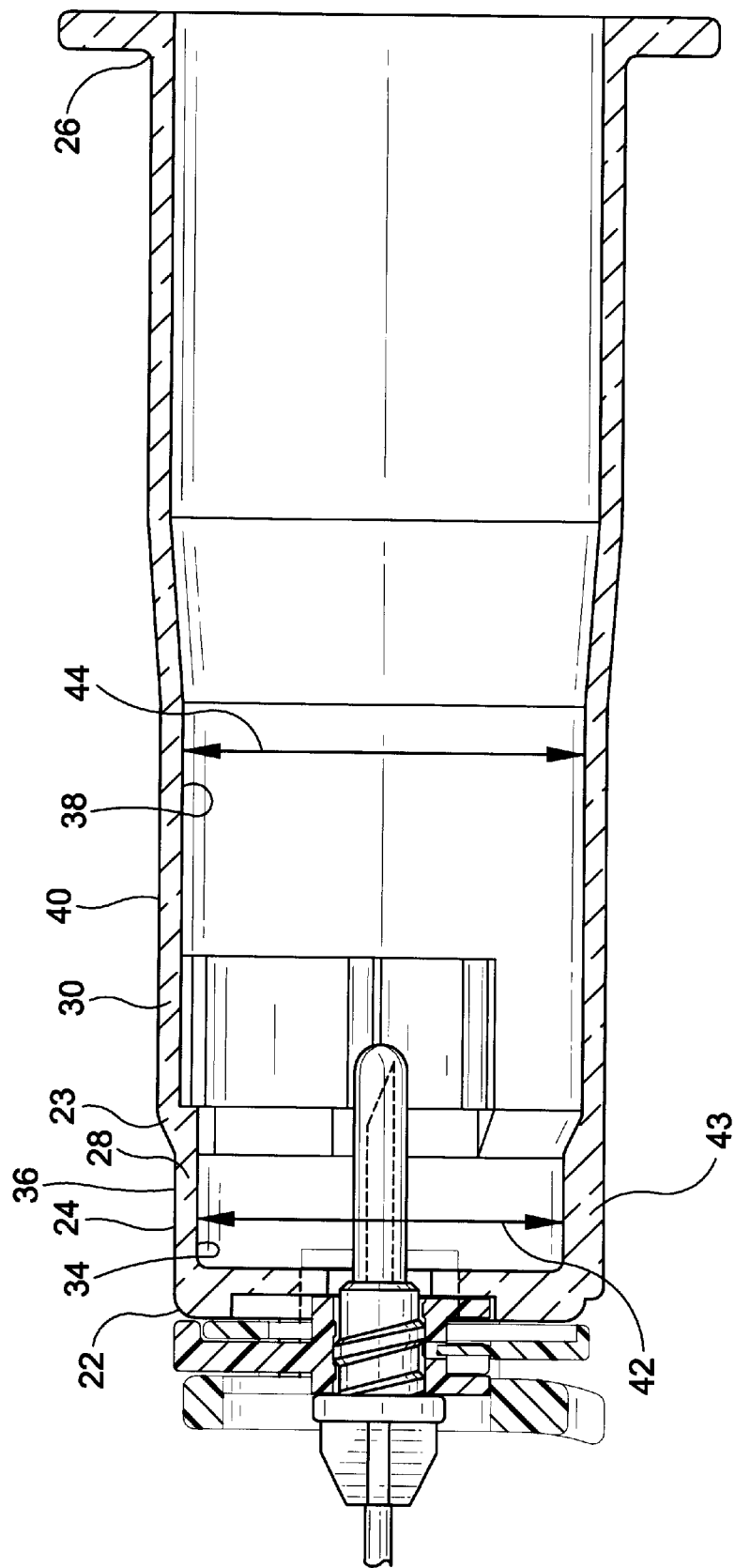
FIG. 5 is a cross sectional side view of the assembly of FIG. 4 taken along lines 5—5.

As shown in FIGS. 1 and 5, housing 20 has a top end 22, an upper section 24, and a bottom end 26. A first sidewall 28 extends from top end 22 to a shoulder 23 and a second sidewall 30 extends from shoulder 23 to bottom end 26. First sidewall comprises an inner surface 34 and an outer surface 36 and second sidewall comprises an inner surface 38 and an outer surface 40. The inner diameter 44 of second sidewall 30 is larger than the inner diameter 42 of first sidewall 28.

Figure 6:
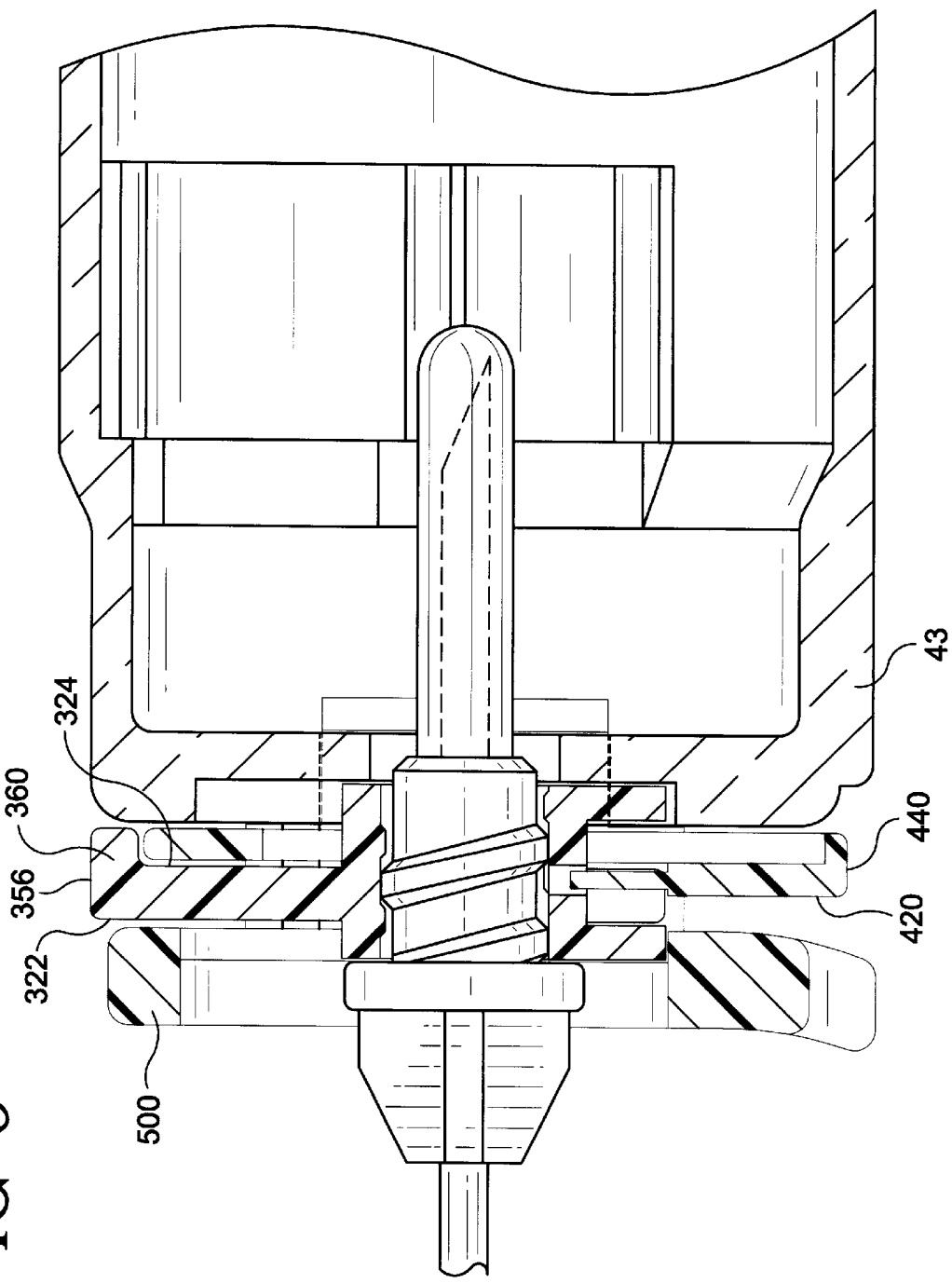
FIG. 6 is an exploded cross sectional side view of the assembly of FIG. 5.

As shown in FIGS. 5 and 6, a projection 43 is integrally formed on outer surface 34 of the first sidewall.

As shown in FIG. 15, the holder further includes a sleeve 50 removably inserted in the bottom end of the housing. Sleeve 50 comprises a body 52 and flange 54. Flange 54 extends outwardly from the rearward end 56 of the sleeve to support the holder on a flat surface and also to provide the user with a means for gripping the holder.

Figure 12:
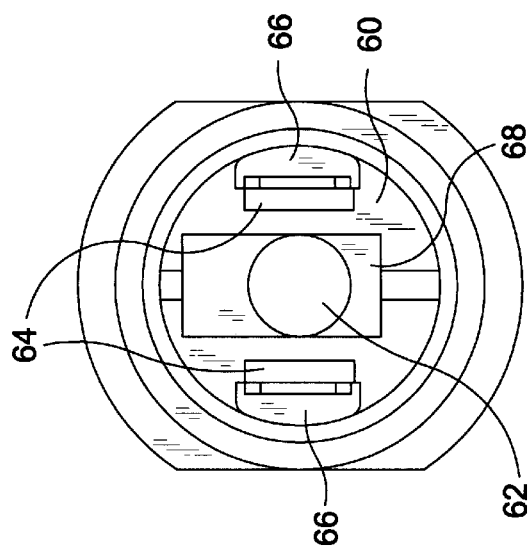
FIG. 12 is a top view of the holder of FIG. 1.

As shown in FIG. 12, at top end 22 of the housing there is a top surface 60. At top surface 60 there is an aperture 62, a pair of side openings 64, a pair of projecting guide arms 66 that extend upwardly from the top surface and a recessed surface 68 surrounding the aperture.

Figure 9:
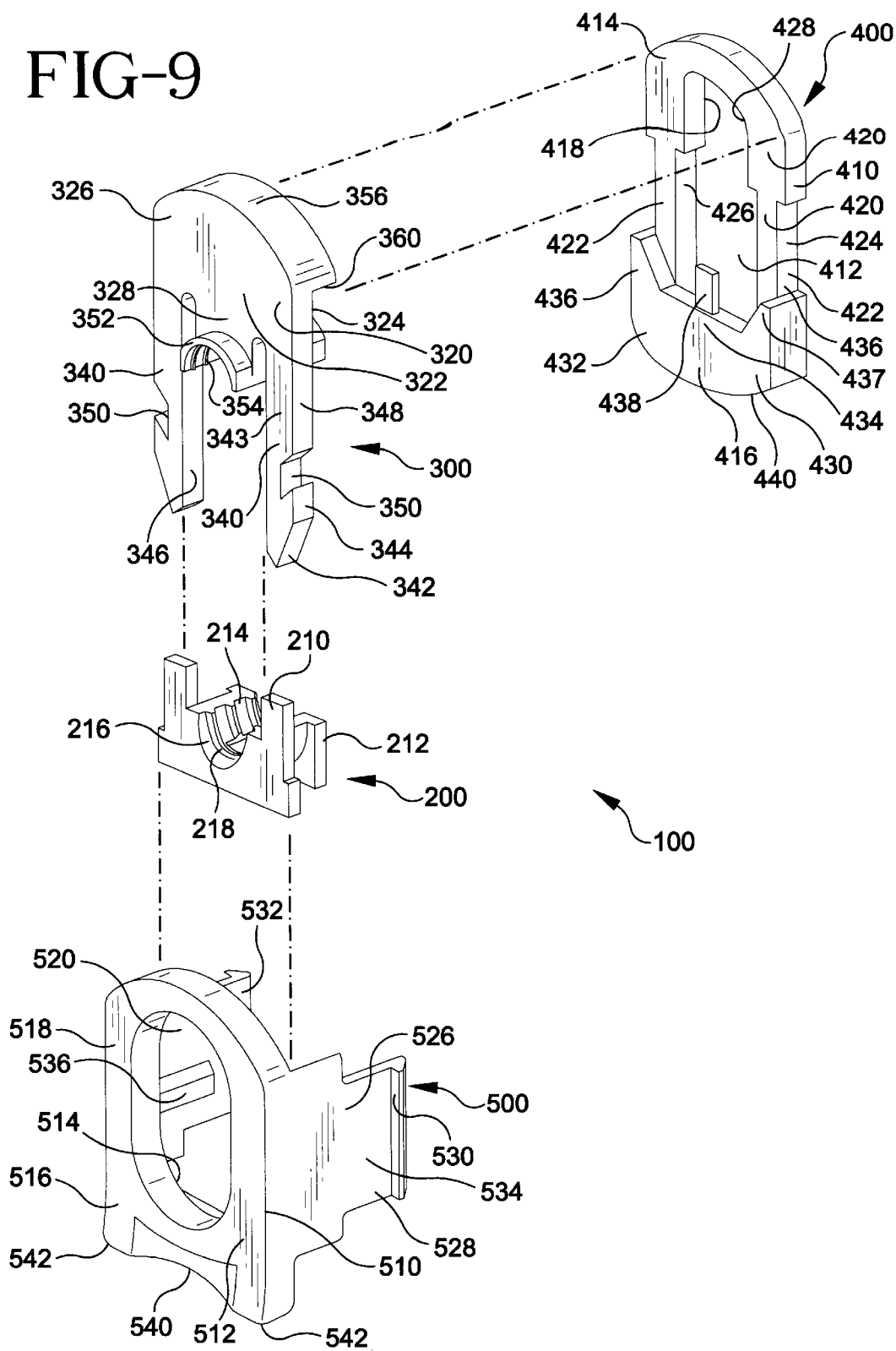
FIG. 9 is a perspective view of the components of the actuation mechanism.
Figure 10:
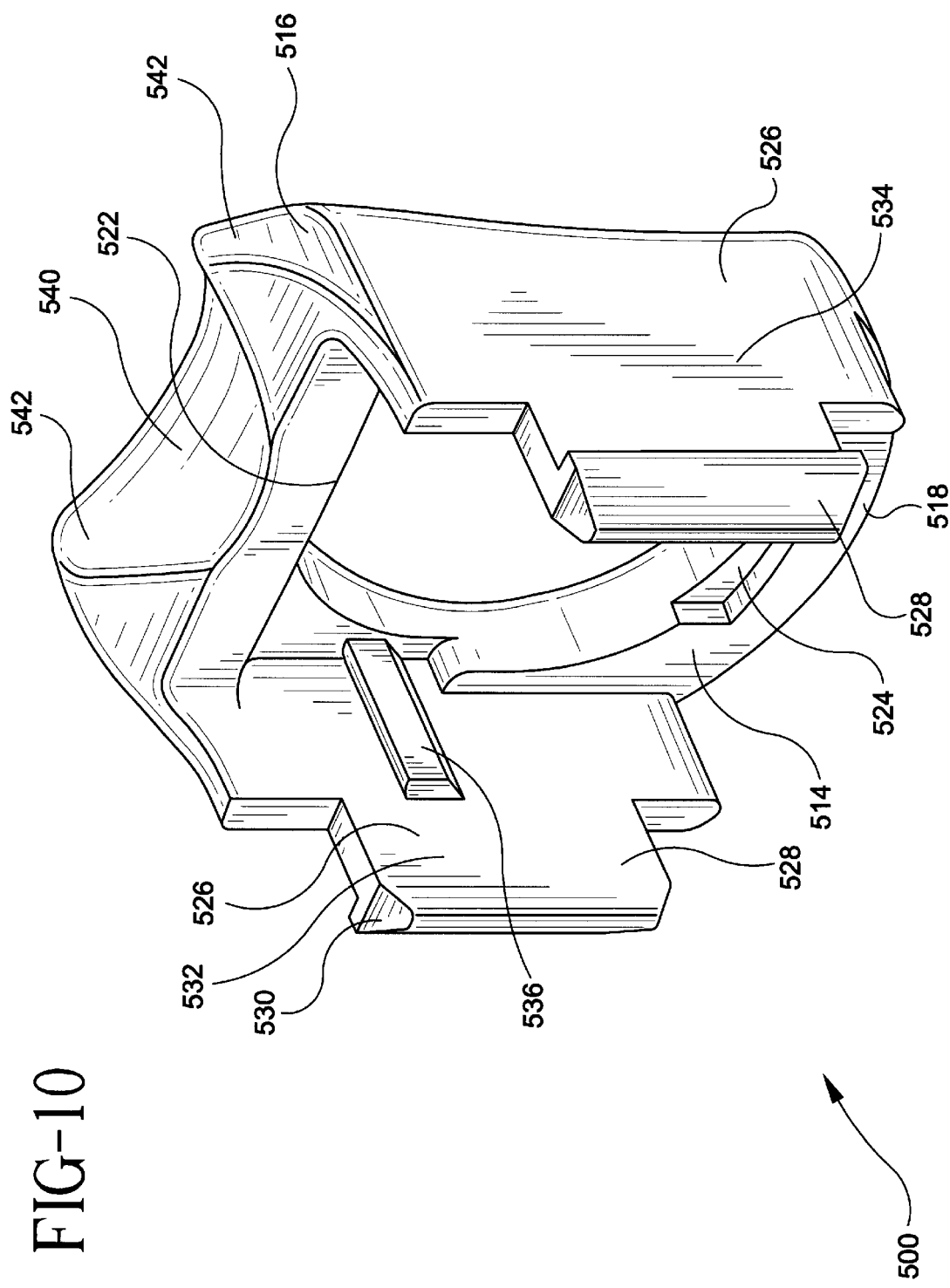
FIG. 10 is an exploded perspective view of the frame of actuation mechanism.
Figure 11:
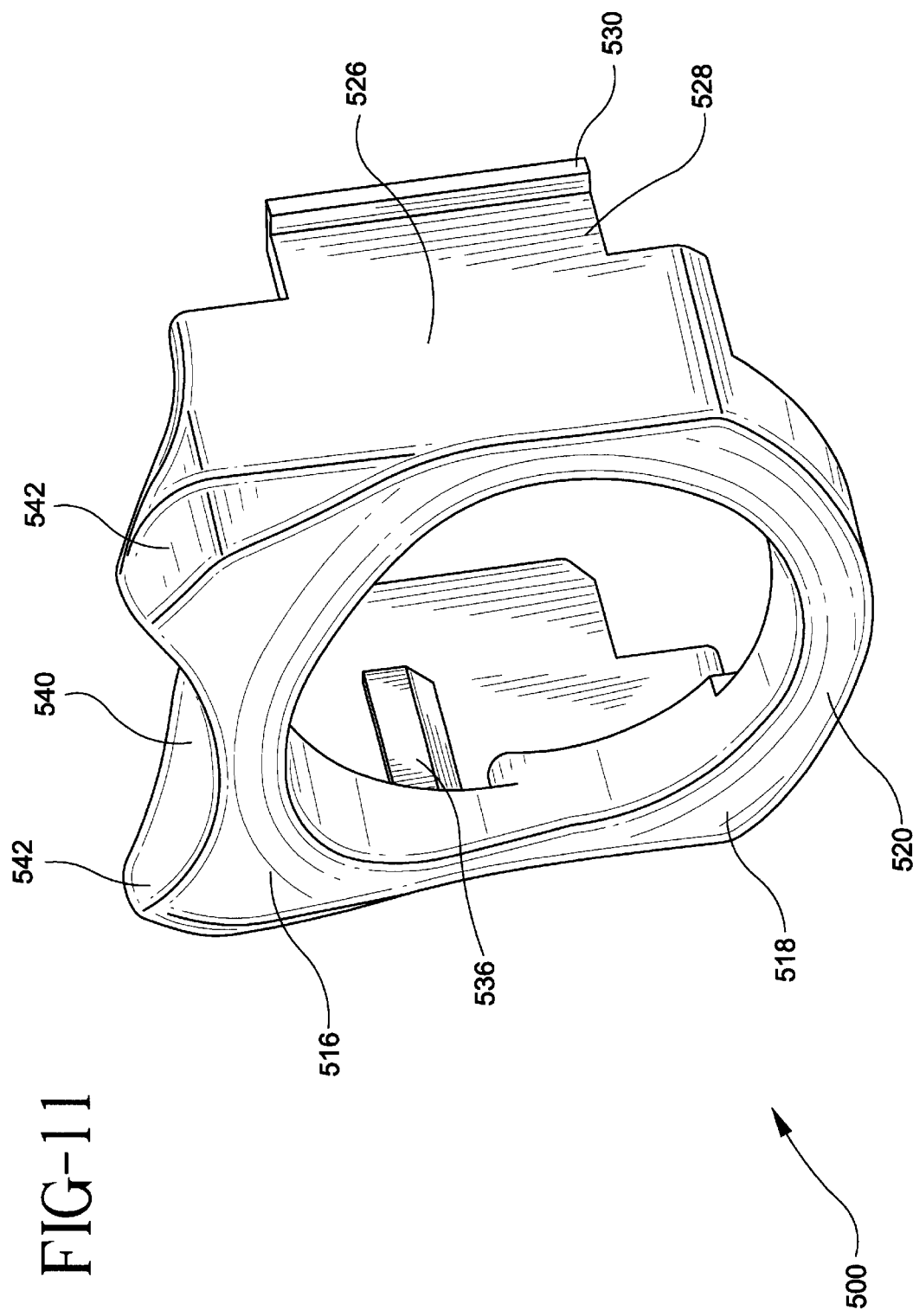
FIG. 11 is an exploded perspective view of the bottom view of the frame of actuation mechanism.
Figure 14:
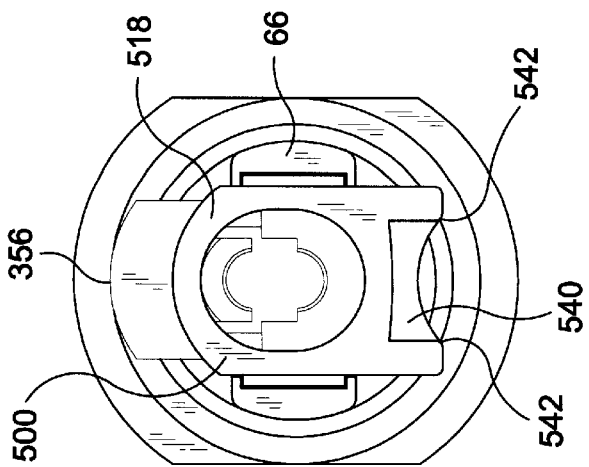
FIG. 14 is a top view of the holder assembly in the open position without a needle assembly of FIG. 6.
Figure 13:
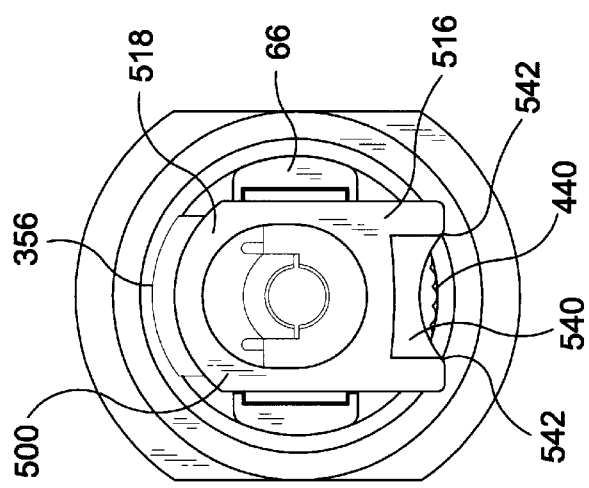
FIG. 13 is a top view of the holder assembly in the closed position without a needle assembly of FIG. 4.

As shown in FIGS. 1 and 9, actuation mechanism 100, includes a retainer 200, a first slider 300, a second slider 400 and a frame 500.

As shown in FIGS. 1 and 9, retainer 200 includes a bottom platform 210, an upper platform 212 and a half female member 214 extending between the bottom and upper platforms. Bottom platform 210 has a larger surface area than upper platform 212. Half female member 214 includes an opening 216 and threads 218.

As shown in FIGS. 1, 6 and 9 first slider or engaging trigger 300 includes a body 320 comprising a top surface 322, a bottom surface 324, a rearward end 326 and a forward end 328. A pair of arms 340 extend from the forward end of the body. Arms 340 each include a forward end 342, a rearward end 343, an inner surface 346 and an outer surface 348. At the rearward end 342 of each arm is a hook 344 and on the outer surface of each arm is an indentation or groove 350. A half female member 352 extends from the rearward end of the body and includes threads 354. Rearward end 326 includes a finger guide 356 and on bottom surface 324 of the body at rearward end 326 is a downwardly extending flange 360.

As shown in FIGS. 1, 6 and 9, second slider or disengaging trigger 400 includes a frame 410 that surrounds a cavity 412. Frame 410 includes a forward end 414, a rearward end 416, a bottom surface 418 and an upper surface 420. Sidewalls 422 extend between the forward end and the rearward end of the frame. Sidewalls 422 include an outer surface 424 and an inner surface 426 and an indentation or cutout 436 on the outer surface of each sidewall. Cavity 412 includes a stopping end 428 at forward end 414. At rearward end 416 on upper surface 420 is a raised ledge 430. Raised ledge 430 includes a rearward end 432 and a forward end 434. At forward end 434 are two opposing projections 437 and a lug 438 located between the projections. At rearward end 432 there is a finger guide 440 for providing the user with finger identification for locating and using the disengaging trigger. Finger guide 440 is distinct from finger guide 356 of the first slider so that the user may easily distinguish the disengaging trigger from the engaging trigger. The finger guides may be structurally distinct as well as color coded. For example, the finger guide for the disengaging trigger may be green and the finger guide for the engaging trigger may be blue. Sidewalls 422 further include cutouts 436 on the outer surface of each sidewall.

As shown in FIGS. 1, 6, 9, 10, 11 and 12 frame 500 includes a top wall 510 comprising a top surface 512, a bottom surface 514, a forward end 516, a rearward end 518 and a bore 520 surrounded by top surface 512. At bottom surface 514 at forward end 516 is a recess 522 and at rearward end 518 is another recess 524. Extending downwardly from top wall 510 are a pair of guidewalls 526. Extending downwardly from guidewalls 526 are feet 528 with hooks 530. Guidewalls 526 include an inner surface 532 and an outer surface 534. On inner surface 532 are protrusions 536. At forward end 516 is a recess indicator 540 that extends into indicator guides 542. Indicator guides 542 extend radially forward and at an incline upwardly from forward end 516 and recess indicator 540.

The four parts of the actuation mechanism 100, retainer 200, first slider or engaging trigger 300, second slider or disengaging trigger 400 and frame 500, are arranged relative to each other in the manner shown in FIGS. 1, 6, 7, 8 and 9.

Figure 7:
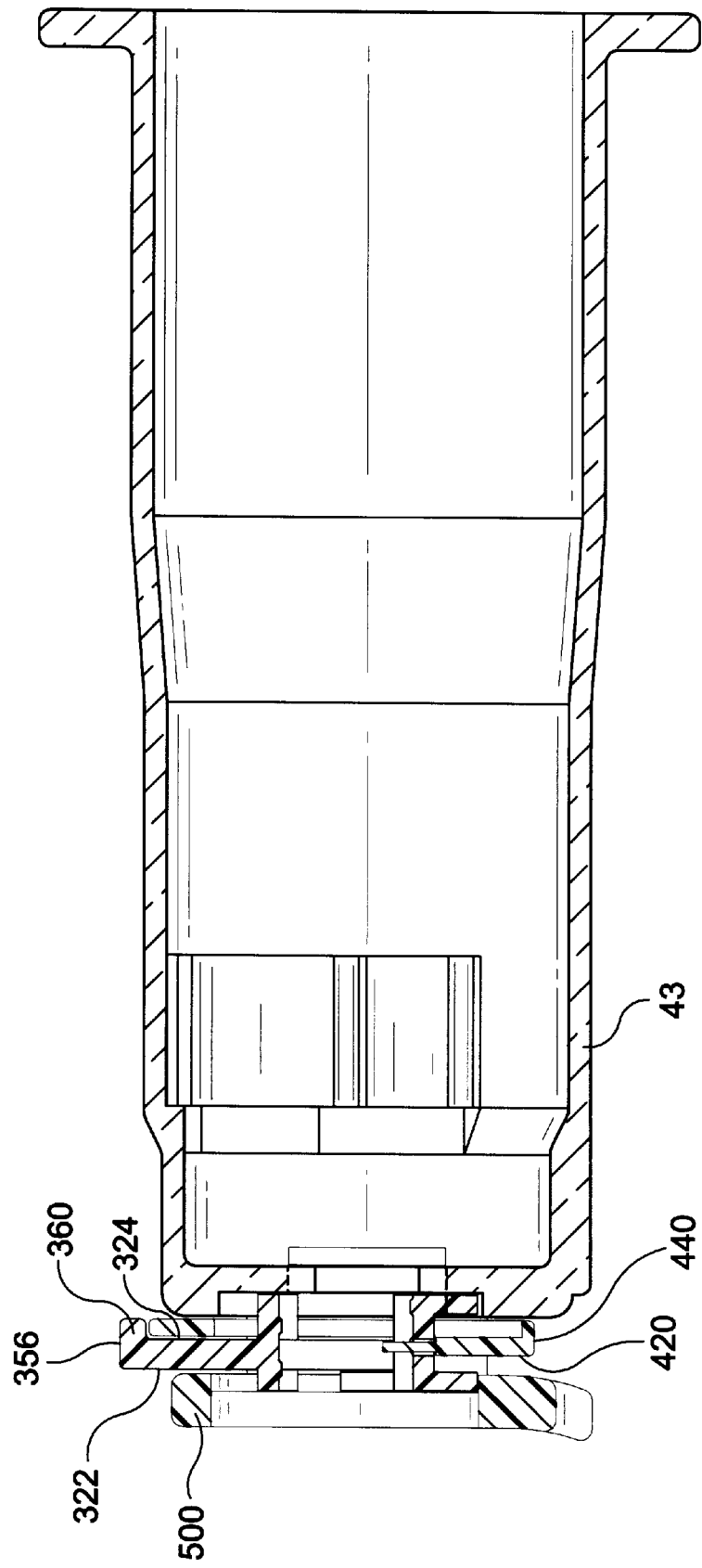
FIG. 7 is a cross sectional side view of the assembly of FIG. 4 taken along lines 7—7 without the needle assembly and with the actuation mechanism in the open position.
Figure 8:
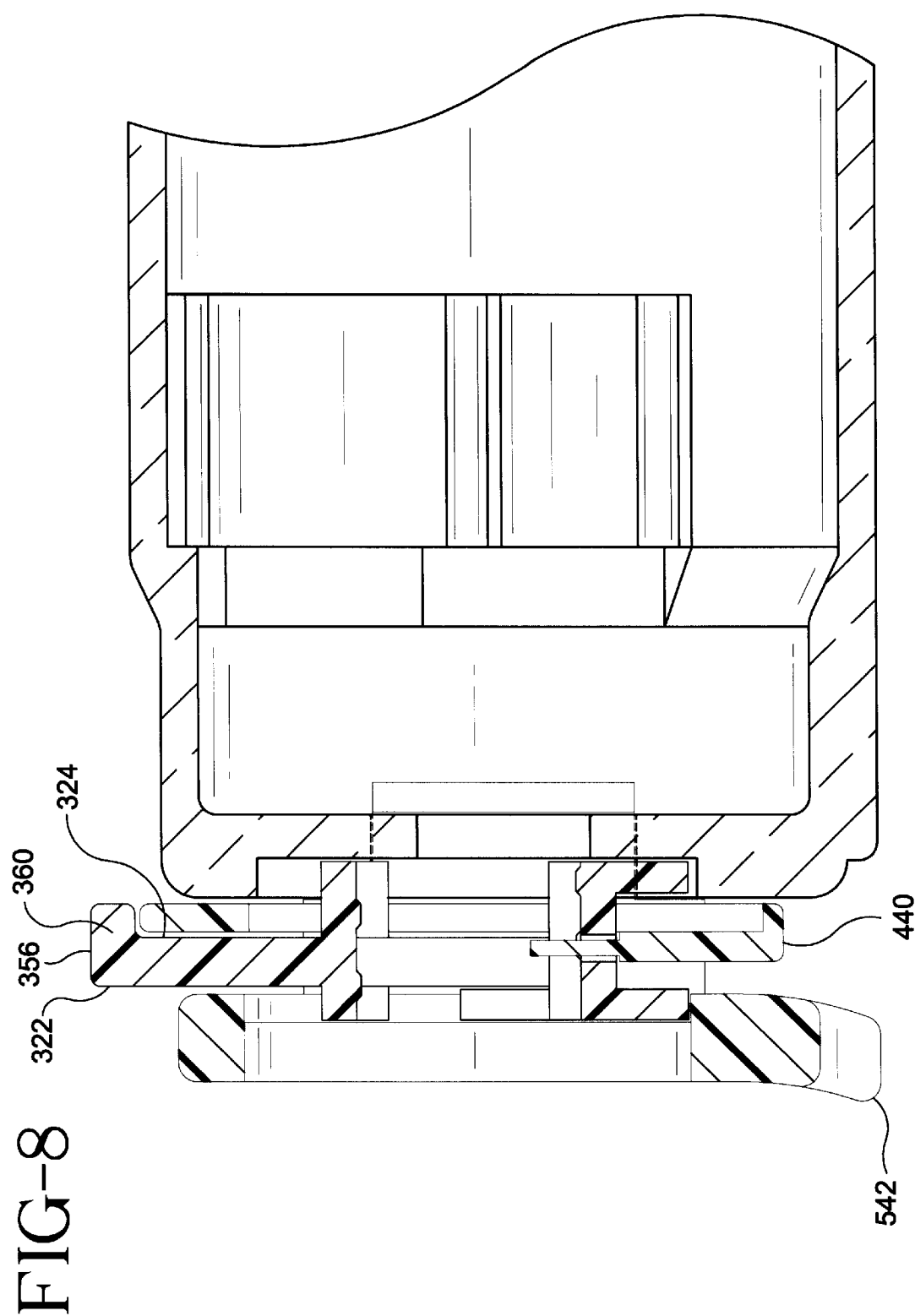
FIG. 8 is an exploded cross sectional side view of the assembly of FIG. 7.

As shown in FIGS. 6, 7 and 8, retainer 200 fits with forward end 516 of frame 500 in recess 522. First slider 300 is associated with the rearward end of frame 500 whereby the top surface 322 of the first slider faces bottom surface 514 of the frame and indentations 350 of the first slider engage with protrusions 536 of guidewalls 526. Half female member 352 of the first slider faces half female member 214 of retainer 200 to from a threaded passageway where the hub of a needle assembly is engaged.

Cavity 412 of second slider 400 surrounds half female members 352 and 214 of the first slider and retainer respectively. Lug 438 fits within opening 216 of half female member 214 of retainer 200.

The actuation mechanism is then secured to top surface 60 of holder 10, whereby hooks 530 of feet 528 of the frame engage with pair openings 64 in the top surface of the holder. The projecting guide arms 66 in the top surface of the holder are to assist in guiding the attachment of the actuation mechanism to the holder.

Figure 16:
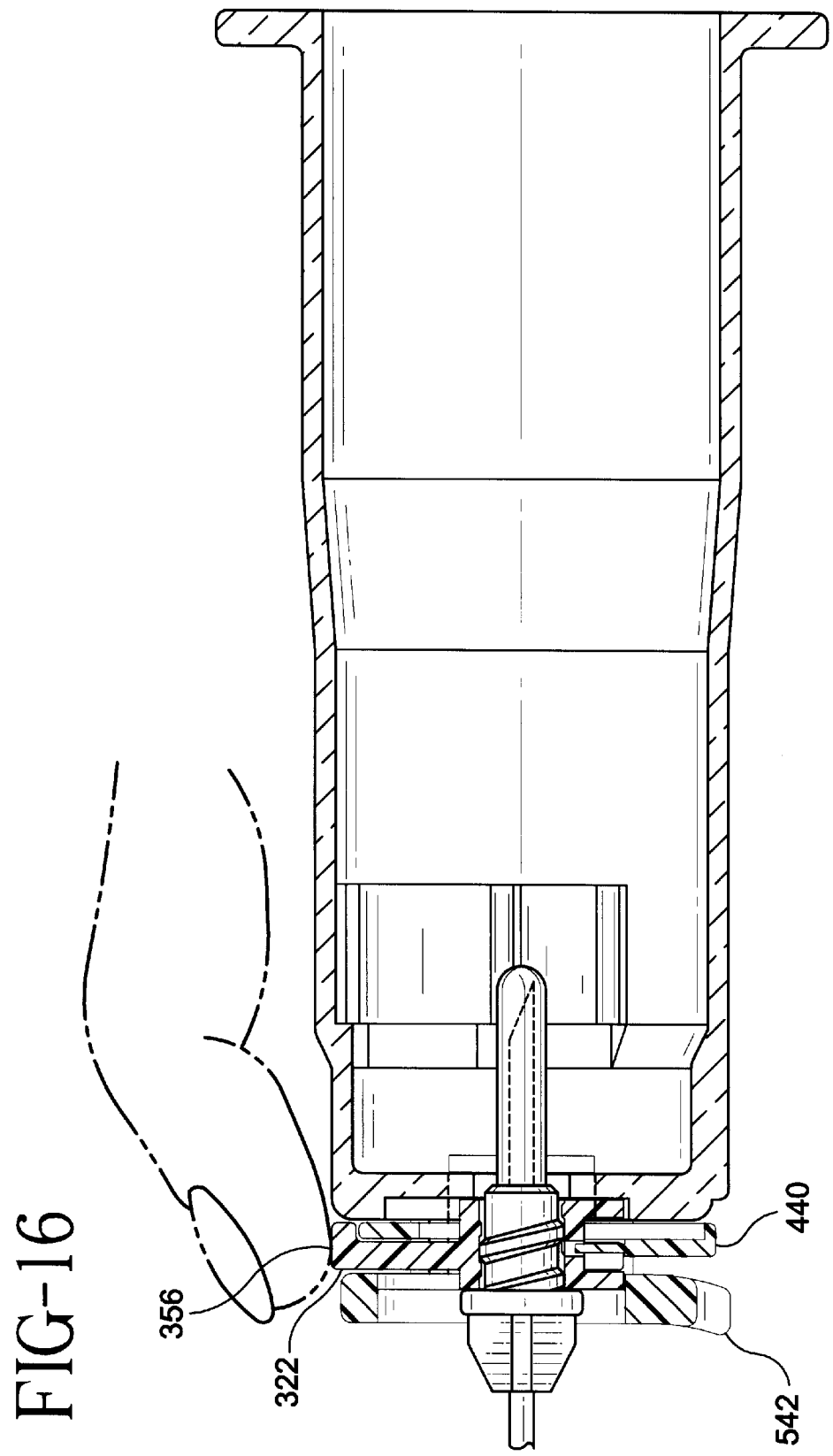
FIG. 16 illustrates the user pushing the first slider to move the actuation mechanism into a closed position.

The actuation mechanism is moved into a closed position when rearward end 326 of the first slider is pushed forward with the user's finger using finger guide 356 as shown in FIG. 16. When there rearward end is pushed forward, indentations 350 engage with protrusions 536 of guidewalls 526 and female half member 352 moves to meet with female half member 214 of retainer 200 to form a threaded passageway so that the hub of a conventional needle can be secured in the passageway.

The actuation mechanism is moved into the open position when rearward end 432 of the second slider is pushed forward towards the first slider whereby the user pushes the slider at the finger guide 440. When the rearward end is pushed forward, cutout 436 pushes arms 340 of the first slider so that indentations 350 disengage from protrusions 536 of the guidewalls, and the first slider moves backwards but not beyond the point when stopping end 428 of cavity 412 holds half female member 352 of the first slider.

Figure 17:
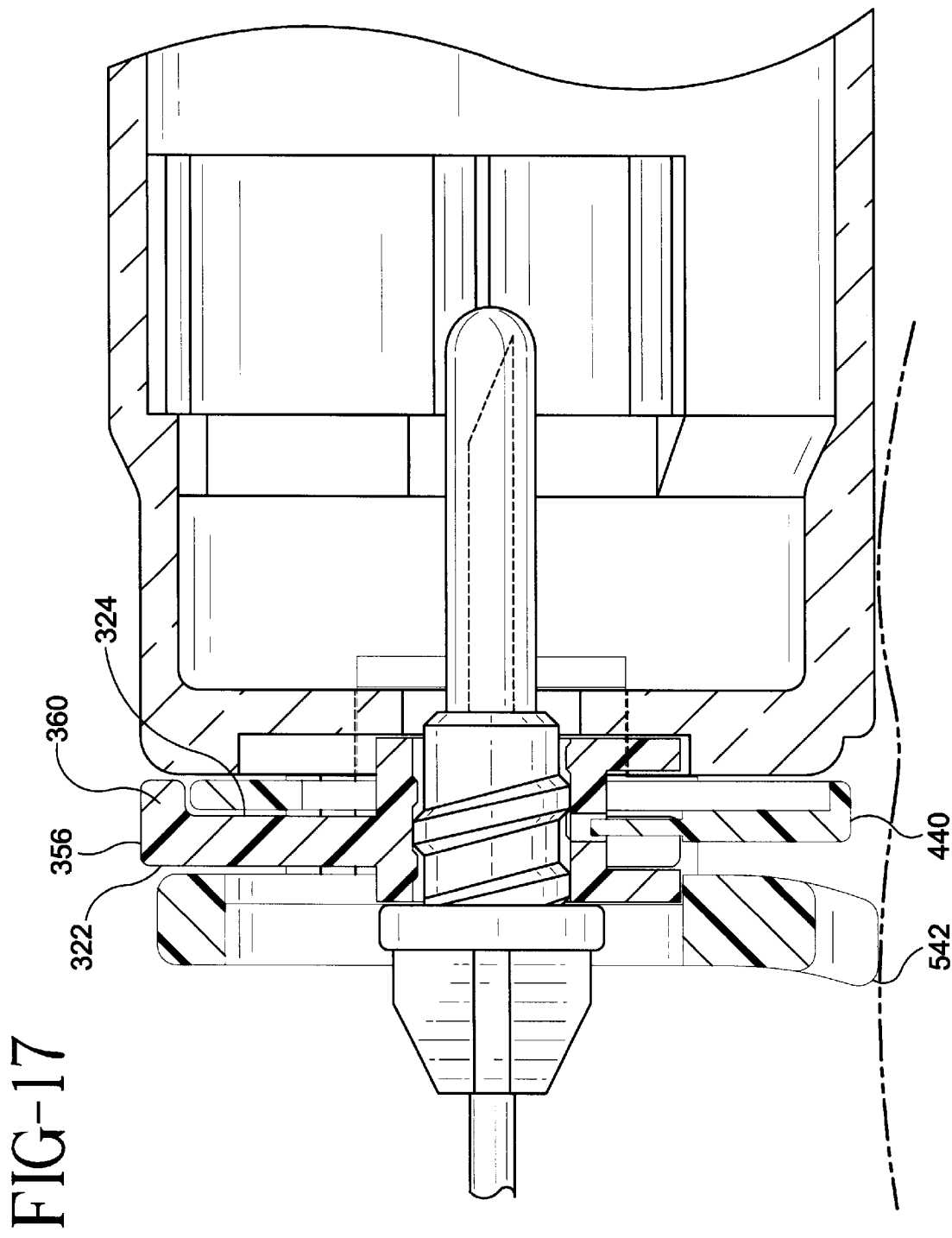
FIGS. 17 and 18 illustrates the benefits of the recess indicators and indicator guides.
Figure 18:
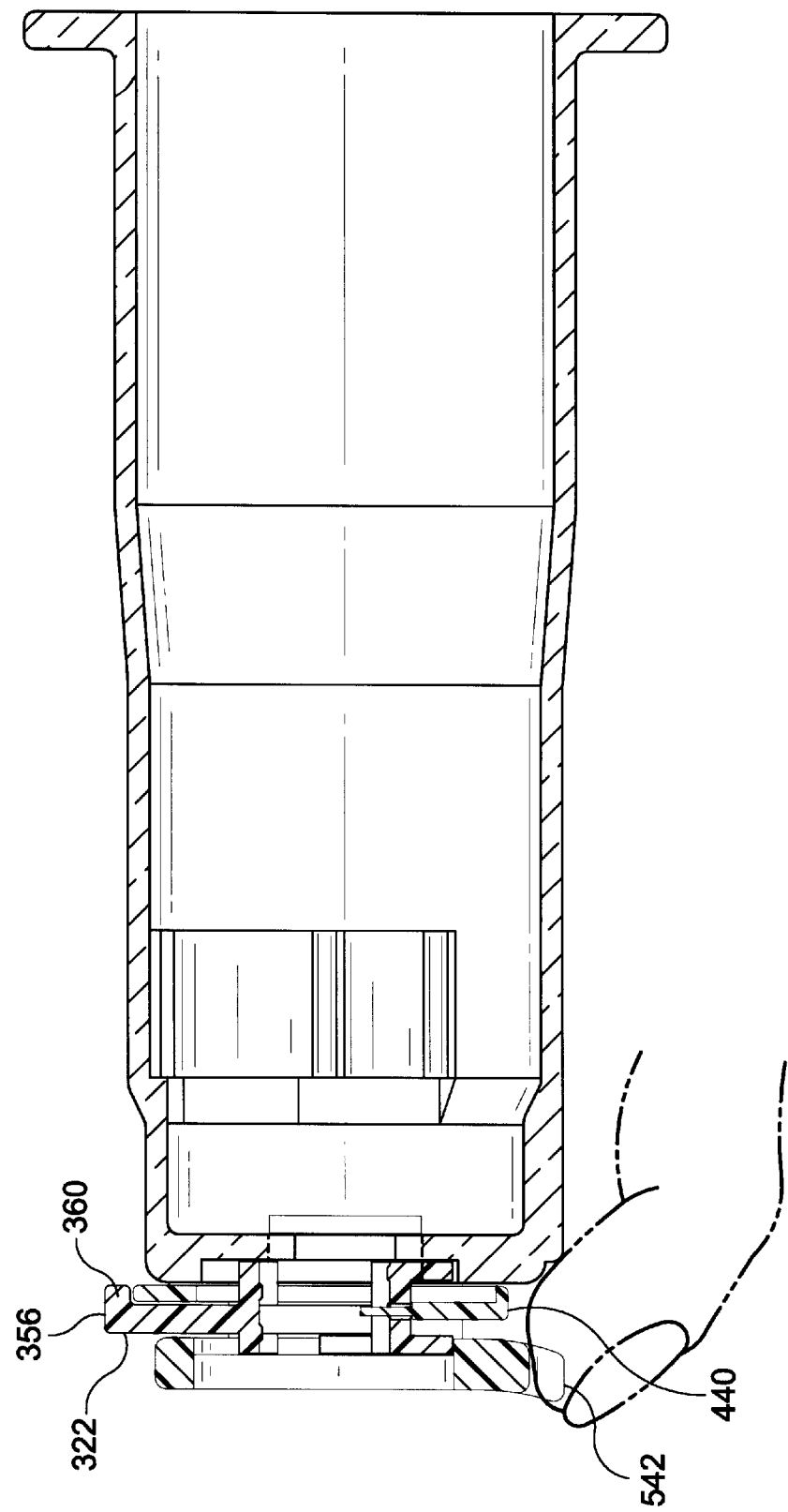

As shown in FIGS. 17 and 18, the recess indicators 542 and indicator guides 542 deter the user from touching the needle and the prevention of premature release of the needle whereby the guides act as a shield between the patient's skin and the disengaging trigger. As shown in FIG. 17, indicator guides 542 rest upon the patient's skin so that the patient's skin does not prematurely trigger disengaging trigger 400 at finger guide 440. In addition as shown in FIG. 18, recess indicator 540 provides the user with notification that the disengaging trigger is near and therefore prevents the user from prematurely activating the disengaging trigger.

What is claimed:

1. A needle holder for use with a needle comprising a cylindrical threaded hub comprising a cross sectional area, said needle holder comprising:
    a tubular body comprising a top end, an open bottom end and sidewall extending between said top end and said bottom end wherein said top end comprises an aperture;
    a threaded passageway located in alignment with said aperture of said tubular body;

a engaging trigger attached to said threaded passageway to engage said threaded needle hub with said threaded passageway comprising a distinct finger indicator comprising a color and a texture;

a disengaging trigger attached to said threaded passageway opposite said engaging trigger to disengage said threaded needle hub from said threaded passageway comprising a distinct finger indicator comprising a color and a texture distinct from said finger indicator of said engaging trigger;

a frame housing for including said threaded passageway, said disengaging trigger and said engaging trigger;

means for aligning and retaining said frame housing, said threaded passageway, said engaging trigger and said disengaging trigger with said top end of said tubular body; and a preventative needle release indicator located on said frame housing wherein said preventative needle release indicator comprises a finger recess and at least one indicator guide, whereby said indicator guide prevents premature movement of said disengaging trigger and said threaded passageway.

2. The needle holder of claim 1, wherein said threaded passageway comprises an open position with an open cross sectional area whereby the open cross sectional area of the threaded passageway is greater than the cross sectional area of the hub of said needle and a closed position with a closed cross sectional area whereby the closed cross sectional area of the threaded passageway is less than the cross sectional area of the hub of said needle.

3. The needle holder of claim 2, wherein said engaging trigger moves said threaded passageway into said closed position.

4. The needle holder of claim 3, wherein said disengaging trigger moves said threaded passageway into said open position.

5. The needle holder of claim 1, wherein said finger recess is between said indicator guides.

6. The needle holder of claim 1, wherein said preventative needle release indicator is located above said disengaging trigger.

* * * * *